United States Patent
Lüth et al.

(10) Patent No.: US 7,346,417 B2
(45) Date of Patent: Mar. 18, 2008

(54) METHOD AND DEVICE SYSTEM FOR REMOVING MATERIAL OR FOR WORKING MATERIAL

(75) Inventors: Tim Lüth, Berlin (DE); Jürgen Bier, Berlin (DE); Angelika Bier, Berlin (DE); Andreas Hein, Oldenburg (DE); Olaf Schermeier, Berlin (DE)

(73) Assignee: LB Medical GmbH, Berlin (DE)

( * ) Notice: Subject to any disclaimer, the term of this patent is extended or adjusted under 35 U.S.C. 154(b) by 486 days.

(21) Appl. No.: 10/472,654

(22) PCT Filed: Mar. 25, 2002

(86) PCT No.: PCT/EP02/03334

§ 371 (c)(1),
(2), (4) Date: Mar. 15, 2004

(87) PCT Pub. No.: WO02/076302

PCT Pub. Date: Oct. 3, 2002

(65) Prior Publication Data

US 2004/0157188 A1    Aug. 12, 2004

(30) Foreign Application Priority Data

Mar. 26, 2001 (DE) ............... 101 14 910
Mar. 28, 2001 (DE) ............... 101 15 170
Apr. 6, 2001 (DE) ............... 101 17 403

(51) Int. Cl.
*G06F 19/00* (2006.01)
*A61B 5/05* (2006.01)

(52) U.S. Cl. .............. 700/117; 433/75; 600/424; 128/920

(58) Field of Classification Search ........... 700/117; 600/424; 128/920; 433/72, 75
See application file for complete search history.

(56) References Cited

U.S. PATENT DOCUMENTS

| | | | |
|---|---|---|---|
| 4,824,367 A | 4/1989 | Rosenstiel et al. | 433/75 |
| 5,017,139 A | 5/1991 | Mushabac | 433/72 |
| 5,257,203 A | 10/1993 | Riley et al. | 364/474.05 |
| 5,281,136 A | 1/1994 | Giannella et al. | 433/76 |

(Continued)

FOREIGN PATENT DOCUMENTS

DE            4304571            8/1994

(Continued)

*Primary Examiner*—Kidest Bahta
*Assistant Examiner*—S. S. Rao
(74) *Attorney, Agent, or Firm*—Norris, McLaughlin & Marcus, P.A.

(57) ABSTRACT

Method and system, for which can be used in the fields of medicine and dentistry as well as for the most varied types of material working in different areas of application and model working, provides that an exact removal of material or a highly precise, reproducible material working can be realized by acquiring, storing and processing data pertaining to position and/or orientation of an effector and their changes relative to the position of at least one reference body. The effector is controlled and/or regulated with regard to its power and/or parameterization based on a predetermined working volume, material volume removed and remaining material volume. A first marking support with markings is arranged on a handpiece with the effector, where the handpiece is connected to a control unit, and a second marking support with markings is attached to the material object or tissue object.

57 Claims, 6 Drawing Sheets

U.S. PATENT DOCUMENTS

| | | | |
|---|---|---|---|
| 5,332,391 A | 7/1994 | Jermyn | 433/76 |
| 5,402,582 A | 4/1995 | Raab | 33/502 |
| 5,408,409 A * | 4/1995 | Glassman et al. | 600/407 |
| 5,575,646 A | 11/1996 | Giannella | 433/76 |
| 5,630,431 A * | 5/1997 | Taylor | 128/897 |
| 5,688,118 A | 11/1997 | Hayka et al. | 433/27 |
| 5,725,376 A | 3/1998 | Poirier | 433/172 |
| 5,989,024 A | 11/1999 | Jonjic | 433/76 |
| 6,000,939 A | 12/1999 | Ray et al. | 433/27 |
| 6,021,343 A | 2/2000 | Foley et al. | 600/429 |
| 6,030,211 A | 2/2000 | Sandhaus | 433/76 |

FOREIGN PATENT DOCUMENTS

| | | |
|---|---|---|
| DE | 19534590 | 3/1997 |
| DE | 19902273 | 8/2000 |
| DE | 4447753 | 11/2000 |
| EP | 0741994 | 11/1996 |
| WO | WO9611624 A2 * | 4/1996 |
| WO | WO98/40030 | 9/1998 |
| WO | WO99/38449 | 8/1999 |

* cited by examiner

METHOD AND DEVICE SYSTEM FOR REMOVING MATERIAL OR FOR WORKING MATERIAL

FIELD OF THE INVENTION

The invention relates to a method and system for removing material or tissue and for treating material or tissue and can be applied in medicine and dentistry as well as for different types of material processing and model working.

The methods of the invention and the system can be applied, for example, to controllably arrange and guide handpieces as well as to switch on and off, to control power to or parameterize the effector in surgery and dentistry for optimally removing tissue in preparation for conservation and for the insertion of implants, inlays and onlays. In addition, high-precision cuts can be set up.

BACKGROUND OF THE INVENTION

Currently, instruments such as drills, cutters and saws, which are inserted in the chuck of a medical handpiece, are mostly used in medicine for removing tissue. Sometimes, laser systems are used which can separate and/or remove soft and hard tissue.

In tissue removal, tissue cuts, tissue openings and tissue cavities or passageways are produced which should satisfy medical criteria (e.g., residual tissue is free of tumors, bacteria, caries, or the residual tissue has a high firmness) and/or additional criteria (e.g., the geometry of the removed tissue has a particular fitted shape for inserting a mating piece).

Coordinate measurement systems that can be used to measure the position (position and orientation) of a tool relative to a reference coordinate system are known from measurement technology.

Medical navigation systems are known from computer-assisted surgery which enable to display the position (position and orientation) of the instrument relative to a patient's tissue after registration of the tissue.

Medical robot systems are also known from robot-assisted surgery whereby the instruments can be moved by a robot on predefined pathways, so that for example a bore can be placed at a certain position (position and orientation) and a cavity with a particular geometric shape can be bored.

In addition, medical interactive systems are known from robot-assisted surgery, wherein the instruments are attached to a passive (actively braking) or to an active (actively driven) mechanism. However, a physician is able to move the instruments manually by directly guiding the instrument or the mechanism inside specified volumes, on specified surfaces and along specified pathways (straight lines, curves), in order to place, for example, a bore at a certain location (position and orientation) or to rebore a cavity with a particular desired geometric shape.

Moreover, medical tele-manipulation systems are known from robot-assisted surgery, whereby the instruments are attached to an active mechanism (slave manipulator), with a physician being able to move the instruments manually via a coupled input mechanism (master manipulator) inside specified volumes, on specified surfaces and along specified pathways (straight lines, curves), in order to place, for example, a bore at a certain location (position and orientation) or to rebore a cavity with a particular desired geometric shape.

Hand scanners, which are able to measure a 3-D-surface model with high accuracy via a streak projection or by other methods, are known in dentistry. A physician has been unable until now to use a manually guided instrument for removing tissue, so that the position and/or the geometry of the removed tissue corresponds precisely to predefined or dynamically specified medical criteria (e.g., the residual tissue is free of tumors, bacteria, caries, or the residual tissue have a high firmness) or geometric criteria (e.g., the residual tissue or the removed tissue has a particular fitted shape for inserting an object).

This is related to the observation that humans lack the ability to precisely orient their hands in a 3-D-reference coordinate system.

Even when using a navigation system, a physician has until now been unable to remove tissue with a manually guided instrument so that the position and/or the geometry of the removed tissue precisely corresponds to predefined or dynamically defined medical criteria (e.g., the residual tissue is free of tumors, bacteria, caries, or the residual tissue has a high firmness) or geometric criteria (e.g., the residual tissue or the removed tissue has a particular fitted shape for inserting an object).

Non-tactile tissue-removing effectors, such as laser beams, don't allow a user who manually treats hard tissue to detect by feel the shape of the removed tissue or the generated fitted shape. Fitted shapes (e.g., cylindrical) that satisfy certain criteria can therefore not be manually produced.

Robot-controlled, tele-manipulated or interactively robot-guided instrument inserts always significantly increase the complexity of the device which adds to its cost.

In addition, the attending medical personnel as well as the nursing staff must have a high level of training and motivation, requiring significant expenses for training and installation. The surgery often takes longer than without the use of a robot.

The patients have to be placed in a immobile position so as to achieve the desired precision when using a robot.

In dentistry, adjoining structures are frequently accidentally injured with a tissue-removing sensor and/or instrument. Even with navigation support, it is not always possible to cleanly shape a cavity. Prefabricated implants cannot be cleanly fitted. It is not possible to prefabricate inlays, onlays or bridges for a later fit. It is not possible to prefabricate a supra-construction so that it later fits perfectly. It is not possible to use high-quality standard inlays, onlays or bridges which are produced by a manufacturer of implants or similar manufacturers. It is not possible to cleanly reshape cavities so that they meet certain medical criteria (e.g., distance from bacteria-infected, tumorous tissue). It is not possible to cleanly reshape cavities so that they meet certain manufacturing criteria (e.g., shaping of the fitted piece for fabrication with three-axes cutters). It is not possible to cleanly reshape cavities so that they meet certain criteria for the integration of fitted pieces (insertion, plug-in, secured against rotation). It is not possible to cleanly reshape cavities so that they meet a combination of these criteria. It is not possible to measure and store manually removed tissue (e.g., on a model), and to use the removed tissue as a "template" for a tissue removal with identical shape on the same or on another object (e.g., a patient's tissue).

In soft tissue surgery cuts cannot be placed so as to correspond to certain medical criteria (e.g. distance to bacterial, tumorous tissue) and/or criteria for integrating transplants and implants (e.g., breast implants after tissue removal).

In knee endoprosthesis, multiple cuts cannot be produced without fixing or kinematic guiding with cleanly defined cut surfaces.

In spinal surgery, decompressions and pedicle screw insertion cannot be performed without fixing the tissue and/or kinematically guiding the instruments.

Another disadvantage of conventional solutions is that the navigation systems according to the state of the art cannot use tools whose transformation matrix is not known ahead of time. This limits the user to a tool set from a particular company. The user is unable to calibrate a new tool without problems. At least the push of a button is needed for calibration. If the tools of an instrument, such as for example a handpiece, are changed, there is a risk that an unregistered tool is being used. This can results in injury to the patient, since the position and angle values can be in error without being recognized as erroneous.

Handpieces, in particular for computer-assisted dentistry, are described in various publications. Two methods currently exist in dentistry which require marking the handpiece for a three-dimensional reference, namely on one hand manual drilling with navigated position orientation and, on the other hand, drilling with a kinematic mechanism, e.g. a robot.

U.S. Pat. No. 4,824,367 describes the device for displaying the parallel alignment of a dental handpiece, consisting of an angle sensor for generating electrical angle signals which indicate the orientation of a cutter that is operated with a dental handpiece, adjusting elements for adjusting electrical reference signals which indicate the position of a preset axis, warning elements which emit warning signals if the angle signal is outside a preset range.

U.S. Pat. No. 5,017,139 describes the device with a dental/medical surgical tool for obtaining three-dimensional contour information, consisting of a plurality of arm segments which are connected with each other sequentially, producing a structure with a front and a rear end, a first attachment element for attaching the first end of the structure to a stationary platform and a second attachment element for attaching a surgical tool at the second end of the structure, a plurality of encoders, whereby each encoder is connected with a corresponding arm segment, to produce an electric signal which displays the position of the individual segments. In this way, the position of the surgical instrument can be continuously tracked.

U.S. Pat. No. 6,000,939 describes a device for precise alignment of dental drills consisting of orientation elements for attachment to a dental handpiece, which generate a signal of the drilling angle, and comparison elements which emit warning signals, if the difference of the angle signals is located outside a predetermined range.

EP 0 741 994 A1 describes a method for visualizing the jaw of a person which includes the following steps: insertion of a device with markers for position measurements into the buccal cavity of the person; acquiring at least one image of the jaw with an imaging method, wherein the markers are also imaged, identification of the markers, wherein for visualization the following acts are performed: attaching a 3-D sensor on the outside of the respective jaw; renewed insertion of the position measurement device in the buccal cavity in the same position as during the acquisition of the image, if the device was removed in the meantime, wherein the device is provided with a 3-D sensor; determining the positional relationship between the 3-D sensor of device and the 3-D sensor on the outside of the jaw; removing the device for position measurements, generating a superposition of the optical image of the jaw with the data set in the proper positional relationship. Truppe describes the method also for visualizing a model of the jaw and/or for visualizing the model of the jaw and the jaw. Truppe also describes a method for visualizing the jaw or a model of the jaw, whereby in addition a photographic or video image of the jaw or of the model is produced, which is superimposed with the image obtained with the imaging method.

Ultrasound, optical or mechanical sensors can be used.

U.S. Pat. No. 5,688,118 describes a system for training dentists to produce cavities in teeth. A human phantom torso is placed in a dentist's chair with a model jaw. The student works with a special training units having a pneumatically driven drill and a handpiece which differ in their configuration and operation or application from a "genuine" treatment unit for treating patients. The position and orientation of the "handpiece" and/or "drill" as well as of a "mirror" can be measured in three-dimensional space with a 3-D measurement system. The system is intended to render three-dimensional images of a model jaw with teeth on a display and to represent the positions of the dental tool held by the student on the display relative to the image data of the phantom. It also has to compute and render the "image" of a dentist's mirror from the model data. It is also intended to shorten the time to train a dentist in the preparation of cavities. It should provide a sound and touch similar to that experienced when drilling a real tooth cavity. The device feeds backs to the student, so that the student can later in an actual treatment situation with a real patient and a real treatment tool properly interpret acoustic, tactile and visual information without navigation help and react accordingly. The student must drill a cavity in an artificial tooth of the phantom by taking into account a dental situation defined in the training concept. The compressed air supply to the pneumatic drive can be regulated with a valve, in order to give the student an acoustic and visual indication of the characteristics of a treatment situation. The power of the drill is reduced when simulating a hard tooth material, and is increased when simulating a soft tooth material. The controller follows in general the programmed geometric model characteristics of the simulated tooth model. For ergonomic reasons, the entire system can have the appearance of a dental treatment system. However, due to its concept and operating mode, the system cannot be used as a treatment system.

U.S. Pat. No. 5,257,203 describes a method for controlling a machine tool for, inter alia, dental modeling work. Such machines represents an excellent addition to the present invention. This machine, however, is not used with patients and is unable to later compensate for undercuts of the cavities on the patient.

U.S. Pat. No. 5,725,376 describes a method for producing drill templates. These methods have a significant disadvantage in that the drill template is difficult to affix on the mucous membrane of the mouth and a template for guiding the handpiece is placed exactly at the location where drilling occurs. The method can also not be used for producing cavities of arbitrary shape.

DE 19534590 A1 describes a method for ablation of hard tooth material. The laser power is hereby adjusted depending on the distance between the laser handpiece and the tissue. It is not possible to remove tissue with particular geometric characteristics.

DE 199 02 273 A1 describes a device for intra-operatively determining the placement of dental implants in the jawbone with a navigation system that can image the actual implant drilling position in a three-dimensional x-ray and can determine the spatial position with the help of an attached dynamic reference frame, characterized in that the dynamic reference frame consists of at least one fastening element on the teeth and/or the jaw and an associated releasable element with the dynamic reference frame. The method, however, was already in use in 1998 at the Charité and has been published.

U.S. Pat. No. 5,332,391 describes a device for supporting a plurality of dental handpieces, wherein each handpiece has a different angle of the drill axis relative to the normal orientation of the drill axis in the occlusion plane of the teeth, the device consisting of: a holder for guiding a dental handpiece, a connection in the form of a parallel structure with a free end on which a pivot point is secured for holding the orientation of the drill relative to the occlusion plane constant, and elements arranged next to the pivot point for connecting the holder with the pivot point, wherein the holder is detachable.

U.S. Pat. No. 5,989,024 describes an apparatus that cooperates with a driven tool with a longitudinal axis, whereby the apparatus holds the axis of the tool constant when the tool is moved in space, consisting of: an adjustable arm with two ends, a clamping arrangement for attaching the tool at one of the ends, a base at the other end, which can be secured to a workpiece, wherein the arm includes a first section that allows movement along the longitudinal axis of the tool.

U.S. Pat. No. 5,281,136 describes an apparatus for supporting a dental drill consisting of: a movable arm which can be affixed to a stationary reference point, and wherein the arm can be secured to an end of a dental drill, with the arm constructed so as to maintain the axis of the tool constant normal to a predefined work plane, components for stabilizing the head and the jaw of the patient, consisting of a head support which can be secured to a chair and elements for fixing the jaw on the head support.

U.S. Pat. No. 5,575,646 describes a device for supporting a dental drill consisting of: a support, an arm with two quadrilateral elements which are connected with each other in series while one of the quadrilateral elements is connected with the bearing and another with an element which holds a dental drill instrument, so that the axis of the drill instrument remains constant, an adjusting element for adjusting the direction of the work axis, wherein the bearing is provided with attachment elements for connection with the back support of a chair, wherein the quadrilateral elements are oriented with respect to each other at an angle of 90 degrees, so that one element is located above the patient and another in front of the patient.

U.S. Pat. No. 6,030,211 describes a guiding apparatus consisting of: a carriage which is secured at one point, an intermediate element, which is secured on one end on the carriage and can be moved in a first longitudinal coordinate z, and another end for receiving a connecting arm via an articulated joint, a working head disposed on the connecting arm and holding an instrument holder and two elements for moving the instrument holder along two additional longitudinal axes x and y, whereby the instrument holder is movable in x, y, z and a rotation axis.

WO98/40030 describes a system for transmitting the simulated position of dental implants from an x-ray machine to a robot which can be used to drill into an impression of the patient's jaw. The system includes a mechanical support as well as elements for fastening the impression on the support in a reproducible position. The impression includes at least two rectangular elements that are visible in an x-ray image.

The present state of the art offers no possibilities to provide the handpieces of the dentist at a later time with a marker when only small modifications are made, so that the handpieces can be easily used with a navigation system. Special handpieces exist for this application, which however have to be acquired by the dentist at a substantial cost. They cannot be used with normal turbines and the handpiece cannot be easily separated from the turbine.

Accordingly, the dentist has to have in inventory both "normal" and "navigatable" hand pieces.

SUMMARY OF THE INVENTION

It is an object of the invention to obviate the known disadvantages of the prior art and to provide a method and a system which allows a user to controllably remove and process material or tissue, and not to remove too much or too little material or tissue during the removal. The material or tissue should also be removed very accurately at the correct location and the system should make it possible to use different tools with one instrument freely and risk-free.

According to an advantageous the invention, material can be removed very precisely or material can be processed very accurately and reproducibly within a short time, by measuring, storing and computer-processing data for positioning and/or orienting the effector and their changes relative to the position of at least one reference body, with the data initiating control commands such that, depending on a predetermined work volume and/or or material removal volume and/or residual material volume, the effector is switched by an on/off-function or the power and/or parameterization of the effector is controlled and/or regulated when the effector is in the on-function.

Multivalent application domains are obtained in that the position and geometry of the attained object surface is measured and stored for additional processing operations on the same object or on other objects.

The method and system for removing material or processing material is based on the observation that material from one object is processed or removed for satisfying at least one criterion and that the power and/or shape and/or position of the arranged and/or guided material-processing or material-removing effector is preferably controlled or regulated so that the position and geometry of the achieved object surface is measured and stored for additional processing operations on the same object or on different objects. Moreover, the time for creating and processing the fitted pieces to be inserted as well as the time between material removal and insertion of fabricated or existing fitted pieces is preferably shortened. The method and system can advantageously be applied, for example, for controllably arranging and guiding of handpieces as well as for switching the effector energy on and off during surgery and in dentistry for optimally removing tissue as a preparation for the conservation and insertion of implants, inlays and onlays. Moreover, cuts can be set up with high precision.

It is possible to position clean, precise cuts with a defined geometry, to set up drilled holes, to cut cavities or stumps, and to measure the movements accurately.

It is possible in dentistry to drill holes for implants freehand as precise as when using a guide mechanism. In dentistry, an inlay, onlay or a bridge can then be prefabricated and the cavities can be formed so that the prepared inlays or onlays fit perfectly in the cavities or on the stump. This obviates the need for fabricating an inlay or onlay on-site.

Inlays and onlays can be centrally manufactured at a much lower price and with a higher quality. The time between shaping and delivery is significantly reduced.

In dentistry, it is also possible to remove the tissue for medical reasons and to form at the same time in parallel a cavity or a stump for a perfect match with a fitted piece (without undercuts) while retaining most of the tissue. More complicated geometries can also be obtained.

In soft tissue surgery, a perfect tissue separation can be achieved manually when separating complicated tissue structures (visceral surgery), if simultaneously a tissue positioning measurement system is used, for example based on electromagnetic reflectors. Expensive mechanical assemblies for guiding the instruments can then be eliminated. Comparable results can also be achieved by guiding the instruments manually, without using robots. This represents a significant improvement over the current situation. The function performed by medical cutting robots can thereby be almost completely replaced.

During the tissue removal, the geometry of the removed tissue can also be measured and this geometry can then be used several times. This has advantages when transferring model work to other tissue types. Shapes can also be mirror-imaged relative to an axis or as volume models (positive shape, negative shape).

The templates can also be mirror-imaged with respect to one or more axes. Parts of the geometry can be mirror-imaged from negative into positive shapes.

A user can remove tissue with a manually guided instrument so that the position and/or geometry of the removed tissue corresponds to medical criteria that are defined ahead of time or dynamically (e.g., the residual tissue is free of tumors, free of bacteria, does not show caries, or residual tissue has a high degree of firmness) or geometric criteria (e.g. the residual tissue or removed tissue has a particular fitted shape for inserting a matching piece) with a high quality. This compensates for the inability of humans to precisely orient their hands in a three-dimensional reference coordinate system.

In dentistry, prefabricated supra-constructions, inlays, onlays or bridges can be used.

Complicated geometrical shapes can be fabricated manually. CAD data of the removed material can also be created. The geometric data can be used for fabricating implants or for removing transplants. The geometric data can be used for quality control.

In spinal surgery, openings and cut surfaces can be generated manually and more cleanly. In knee endoprosthesis, cut surfaces can be manually prepared more cleanly. Instruments can be significantly better guided in almost all areas of medicine. The method can also be used to prepare a fitted shape, that satisfies certain criteria (e.g. cylindrical), with non-tactile, tissue-removing effectors, such as laser beams, when manually processing hard tissue.

According to another advantageous embodiment of the invention, it is possible to freely work with marked tools by measuring or computing the position T_HAND with a position and orientation of a handpiece with a tool receptor, whereby the transformation matrix between the handpiece and tool receptor HAND_T_SPANN is stored and the transformation matrix between the tool receptor and the tool effector SPANN_T_WERK is known except for a missing positional degree of freedom, such as the length and a registration point P-REG.

Tools that change their geometrical shape over time are always recalibrated. All instruments all always calibrated. With the invention, the calibration process is advantageously not viewed as an obstacle, since no button has to be pushed. The calibration does not require a machine interaction, but instead only touching a point and then waiting for a signal. Accordingly, calibration of a tool can no longer be overlooked. This significantly improves the safety and operability of medical navigation systems when changing tools.

According to another advantage of the invention, conventional handpieces can be employed in the navigation system, wherein the handpiece has at least one opening for later attachment to a marker support and the opening is formed so as to be in formfitting engagement without play with a projection on the marker support when the handpiece and marker support are installed. Alternatively, the handpiece can have at least one projection for later attachment of a marker support, wherein the projection is formed so as to be in formfitting engagement without play with an opening of the marker support when the handpiece and marker support are installed.

DESCRIPTION OF THE DRAWINGS

The invention will now be described hereinafter in more detail with reference to embodiments depicted at least in part in the drawings.

DETAILED DESCRIPTION OF THE INVENTION

Figure 1:
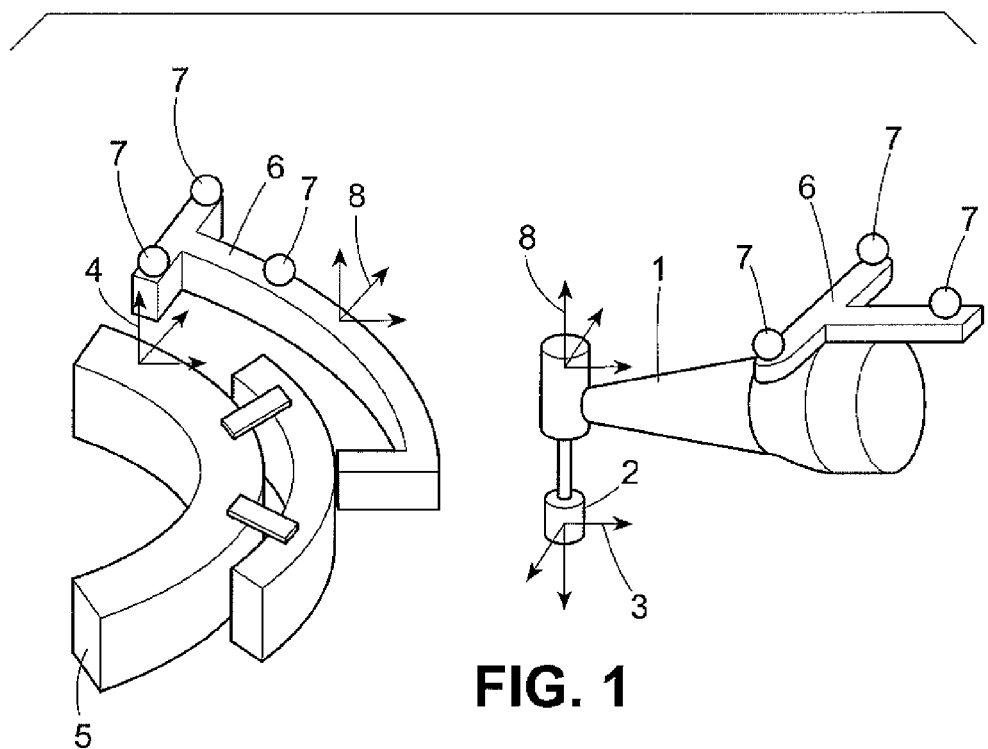
FIG. 1 a tissue-removing effector with a reference position to the tissue object, FIG. 2 an effective geometry and cut geometry in the object, FIG. 3 a fabricated fitted piece and snug fit of the removed tissue, FIG. 4 a visualization of the difference geometry for effector guiding, FIG. 5 an attenuator interval for controlling and regulating the effector power, FIG. 6 a laser handpiece with fitted shape-generating effective geometry body, FIG. 7 the setting of cuts in soft tissue, FIG. 8 a system for manually performing optimal tissue removal, FIG. 9 an instrument handpiece with handpiece markers, FIG. 10 an instrument handpiece with handpiece markers, FIG. 11 an embodiment of the interlock between marker support and handpiece, FIG. 12 an embodiment for fixing and securing the position of marker support and handpiece cone, FIG. 13 an embodiment of the handpiece marker support, and FIG. 14 a handpiece with marker support and markers.

FIG. 1 shows the handpiece of a medical instrument with a tissue-removing effector 2 in a measurable effector position (position and orientation) 3 relative to a reference position 4 of a tissue object 5. The tissue-removing geometry of the effector 2 is known to be almost unchangeable (e.g., cutters, drills) or can be measured and/or adjusted (e.g., laser). The power for removing the tissue can be at least switched on and off, or preferably controlled. The effector 2 can be implemented as a saw blade, a drill, a cutter, a water or particle beam, a laser beam, ultrasound, or as another type of effector for removing tissue. The relative position T_EFF of the tissue-removing effector 3 relative to the reference position 4 T_OBJ of the tissue object 5 can be determined, for example, by a coordinate measurement method based on artificial or anatomic measurement markers located at a known position. FIG. 1 shows marker supports 6 which are secured in a fixed position relative to the effector and/or the tissue object.

As shown in FIG. 1, a marker 7 made of reflecting glass spheres, which are used as signal reflectors in an optical coordinate measurement system, is disposed on the marker support 6.

The marker 7 is in general a set of points, figures or bodies whose position (position and/or orientation) relative to each other as well as relative to the respective marker reference system 8 is known ahead of time and whose position relative to at least one position measurement coordinate system can be determined when needed. Different measurement methods (optical, acoustical, electromagnetic, radar-based, laser-based, line camera, area camera, video sequences, 3-D surface cameras, 3-D laser cameras, 3-D radar processes, etc. with signal transmitting, signal receiving and signal reflecting points, figures or bodies) can be used.

Alternatively, the marker 7 can be implemented as a flange for receiving a measurement sensor in a known position relative to the respective marker reference system 8. The marker 7 can be attached to the corresponding marker support 6 or implemented as a recess and/or can form a part of the geometry of the marker support 6. The respective marker support 6 can also be formed by the handpiece 1 of the effector 2 or by the object itself.

Figure 2:
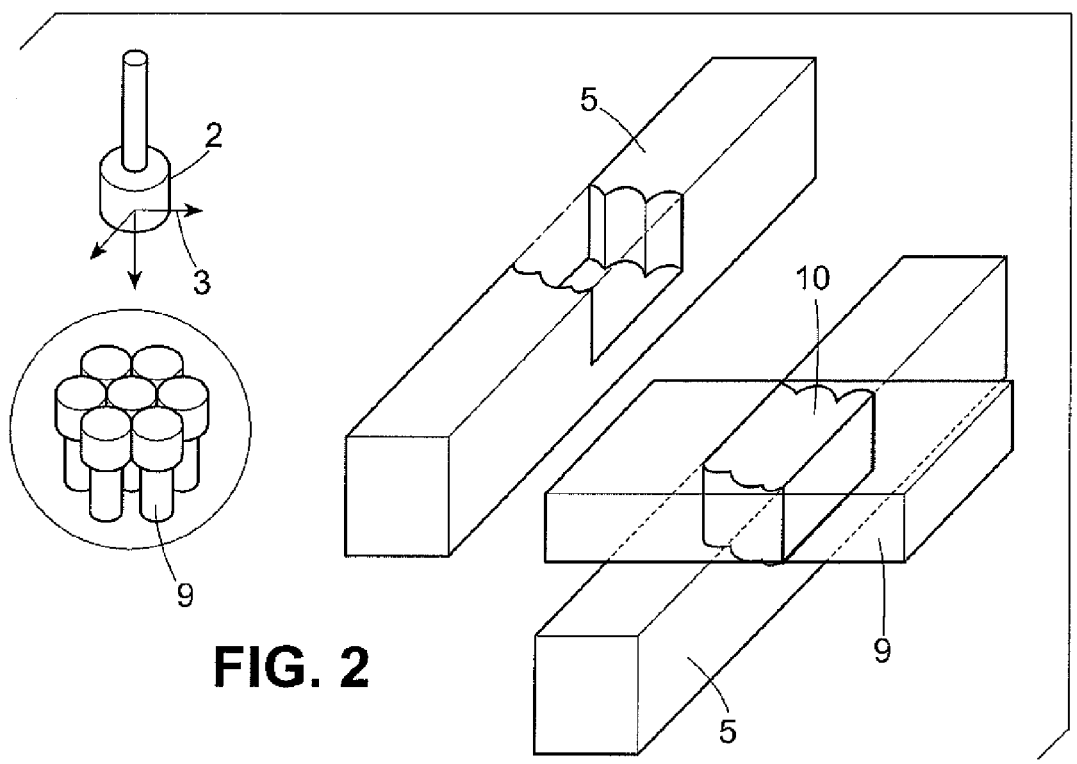

FIG. 2 shows an effective volume or effective geometry 9 which is computed by a spatial superposition of the effector geometry 2 with the measured effector positions 3. The effective volume describes the maximal 3D-geometry scanned by the effector. Also shown is the cut geometry or cut volume, formed from the intersection set of tissue object volume 5 in the reference position 4—before the tissue is removed—and the effective volume 9. The cut volume describes the object volume actually removed by the effector 2. The object tissue geometry relevant for the tissue removal can be generated by a depth-image or volume-image forming method (x-ray, ultrasound, laser, MRT, CT,—or surface image, etc.) or via a surface image generating method (2-D, 3-D surface scanner, video image, hand scanner) or via a tactile or non-tactile distance image generating method (distance laser, tactile measurement sensor, etc.) with subsequent generation of a surface grid. In the simplest case, the non-energized effector geometry 2 contacts the surface and performs a tactile measurement on the surface (by generating a surface grid from the measurement points), or a distance-measuring or surface-measuring sensor is attached to or integrated in the handpiece 1.

The cut volume 10 could represent, for example in dentistry, a drilled, cut or laser-treated cavity in the tooth, in the yaw bone or in a model. The cut volume 10 can in dentistry also describe tissue that has been removed for producing a stump for a crown. Corresponding examples can also be found in surgery. The cut volume 10 can also be an cut surface for separating tissue in hard tissue surgery (osteotomy) or an cut surface in soft tissue surgery (e.g. visceral surgery).

Figure 3:
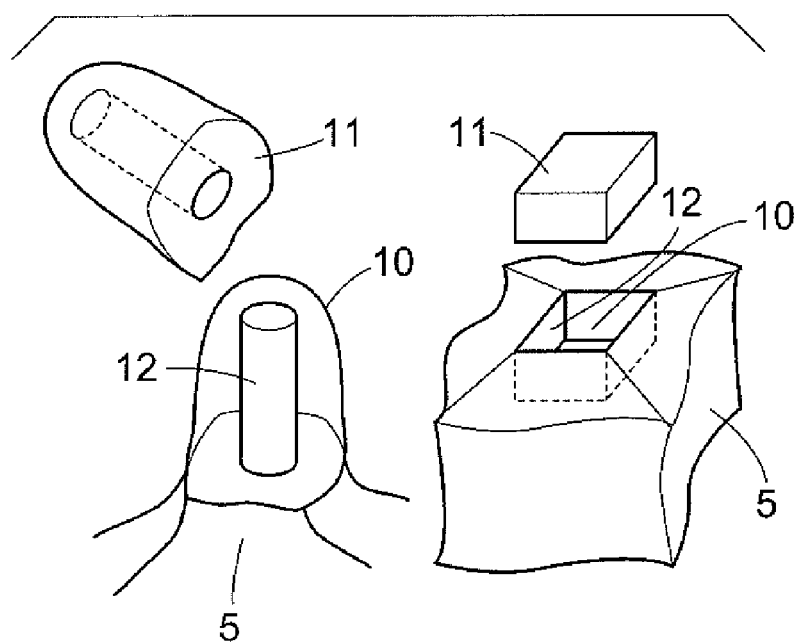

FIG. 3 shows tissue objects 5 with removed tissue volume 10 as well as the geometry of fitted pieces 11 based on the cut volume geometry 10 as well as additional medical criteria and/or criteria for fabricating fitted pieces 11 and/or integration of fitted pieces 11 and residual tissue volume 5, 12. Medical criteria can be, that for example the outside or inside surface of the fitted piece 11 has a minimum distance to the removed tissue 10 or to tissue with certain tissue properties (tumorous, bacterial, hard tissue, spongiosa, outer shell, nerves, organs etc.) or that it must not have traps (cavities) for bacteria. In dentistry, the fitted piece 11 must also satisfy additional medical criteria, such as optimal occlusion (fit between the teeth of different jaws). Other criteria for fabricating fitted pieces may be that the base pieces or materials are available in inventory, or that the fitted pieces 11 can be fabricated with known and/or existing tools or machines, and that these therefore have certain material properties (e.g. firmness/stability or particular geometric shapes). Another criterion can be that the corresponding fitted piece 11 has to be in inventory.

Criteria for integrating fitted pieces 11 and residual tissue volumes 5, 12 can relate to the snug fit between fitted piece 11 and residual tissue volume, i.e. object fitted shape 12, because hard tissue has to be prepared so that the fitted piece 11 can be cleanly fitted. This also required particular geometric shapes. This also includes enlarging or reducing size of the fitted piece, so that a desired final shape is obtained after the residual tissue volume and fitted piece 11 are joined.

The geometry of the fitted piece can also be used to measure, for example a quantity of material or a volume of material and to choose the data for fabricating the fitted piece 11 with the help of a CAD/CAM process and/or by rapid prototyping. For example, a milling machine which mills the fitted piece 11 from a base body, can be controlled. Alternatively, a suitable base body that need only little finishing or no finishing at all, can also be selected and removed from inventory.

Figure 4:
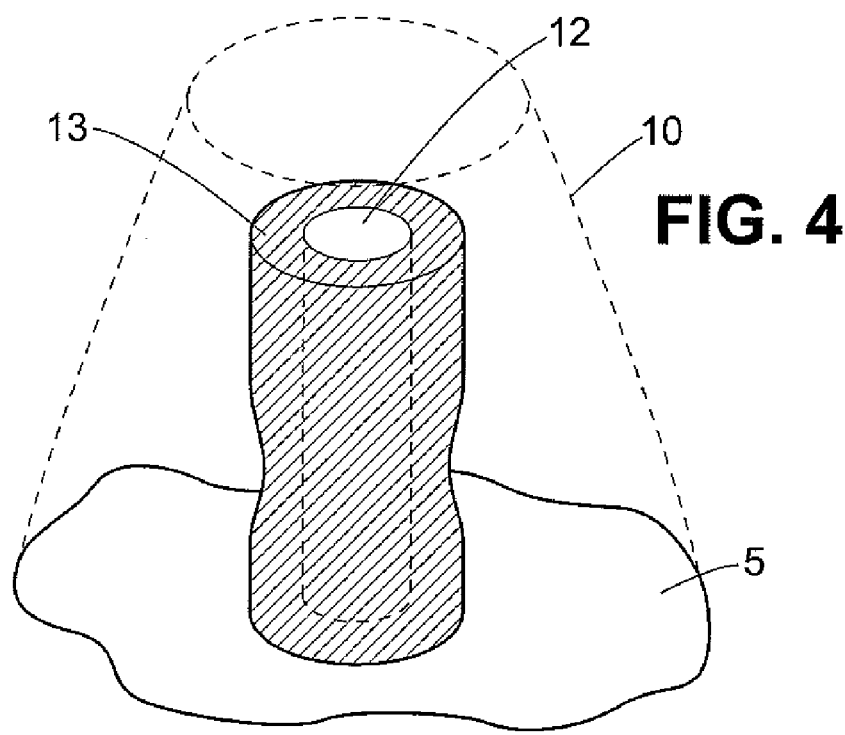

FIG. 4 shows a tissue object 5 (tooth stump) having an optimum filled shape 12 that is already known from the filled piece 11; however, not all the tissue that is to be removed has been removed. The figure shows the difference volume 13, whereby the difference volume is determined from the geometry of the actual filled shape 12 and the actual cut volume 10 by intersecting the two. The difference volume 13 or the difference geometry can be visualized on a display and/or the distance of the effector 2 from the boundary surface difference volume 13 and fitted shape 12 can be indicated acoustically. The visualization can then be used to move the effector either manually (hand-eye and/or hand-ear coordination) or under automatic control (e.g. with a robot) so that the effector should or can reach on tissue of the difference volume 13. This optimally minimizes tissue removal. Since the cut geometry is determined continuously, the system can also be used to measure and document self-generated cavities as well as to further process the measurement data. The effector 2 can also be used as a tactile position measurement sensor head.

Figure 5:
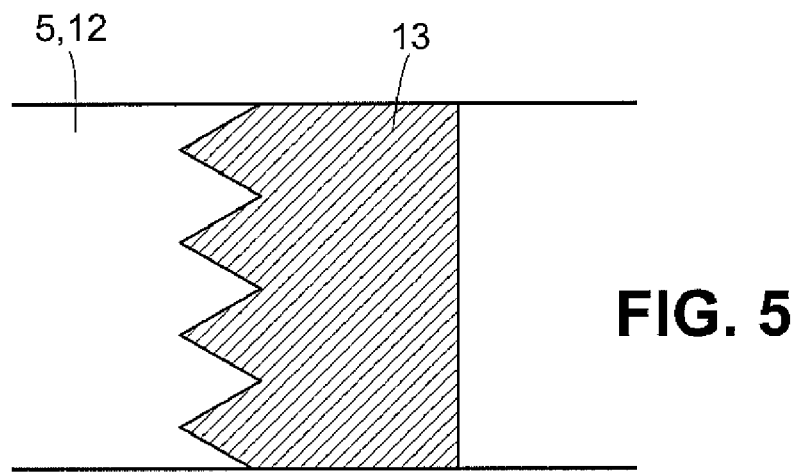

FIG. 5 shows the tissue object 5 and the fitted object shape 12 as well as the difference geometry 13 which describes the tissue still to be removed. The power of the tissue-removing effector 2 is switched off no later than when the effector geometry exits the effector geometry 13 or the joint set of fitted piece geometry 11 and difference geometry 13. The power of the tissue-removing effector 2 is switched on no later that when the effector geometry enters the difference geometry 13 or the joint set of fitted piece geometry 11 and difference geometry 13. The power of the effector 2 is increased depending on the distance from the effector 2 to the object fitted shape 12 and reduced with decreasing distance therebetween. Preferably, the change in power is limited to an attenuation interval starting from the surface of the object fitted shape 12.

Figure 6:
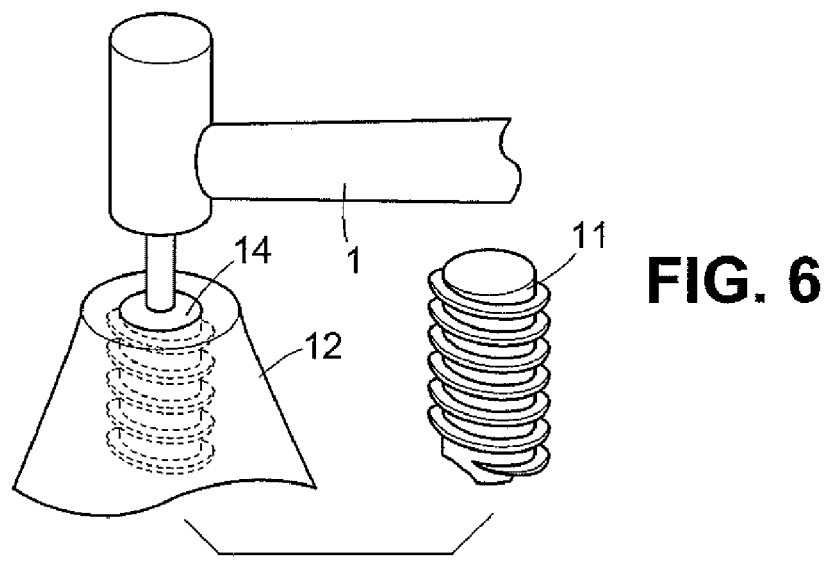

FIG. 6 shows a handpiece 1 (e.g. laser handpiece) with an applied effector geometry body 14, which controllably supplies the tissue-removing energy to the boundary surface so as to form a desired fitted shape 12 for a fitted piece 11. When using a laser and a suitable light-conducting or light-emitting effector geometry body 14, for example, an interior or exterior thread can be cut with the laser so as to be located exactly at the desired location (position and orientation); even the end point of the exiting tread turn to can be known.

Figure 7:
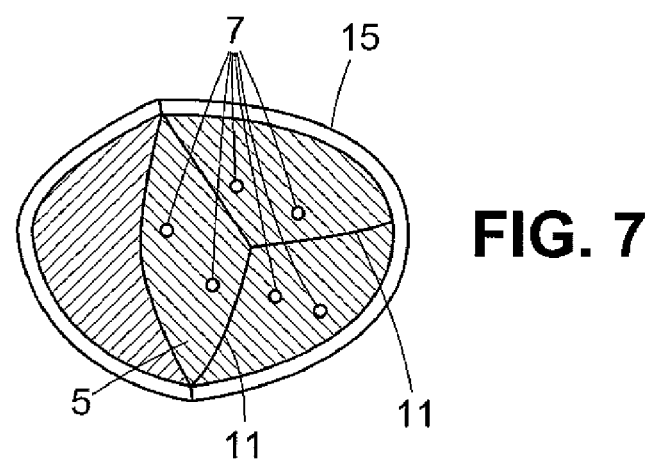

FIG. 7 shows a soft tissue object 5 into which two cuts 11 are to be made, which in this case are to be modeled as fitted pieces. The position of the tissue is determined by markers 7 which are measured, for example, by an electromagnetic position measurement method, similar to a GPS. This method can also be used to determine the position and orientation of partial volumes of the soft tissue. The tissue is preferably located in a dimensionally stable matrix 15, so that the tissue 5 does not move during the separation. The dimensionally stable matrix 15 should retain its shape also when the cuts are set. The matrix could be a foil when using a scalpel effector 2 or a body with a prefabricated, preferably grid-shaped foil, or when using a laser scalpel, a light-transparent, light-conducting foil that lets the laser power exit on the tissue side of the matrix 15 for removing tissue.

Figure 8:
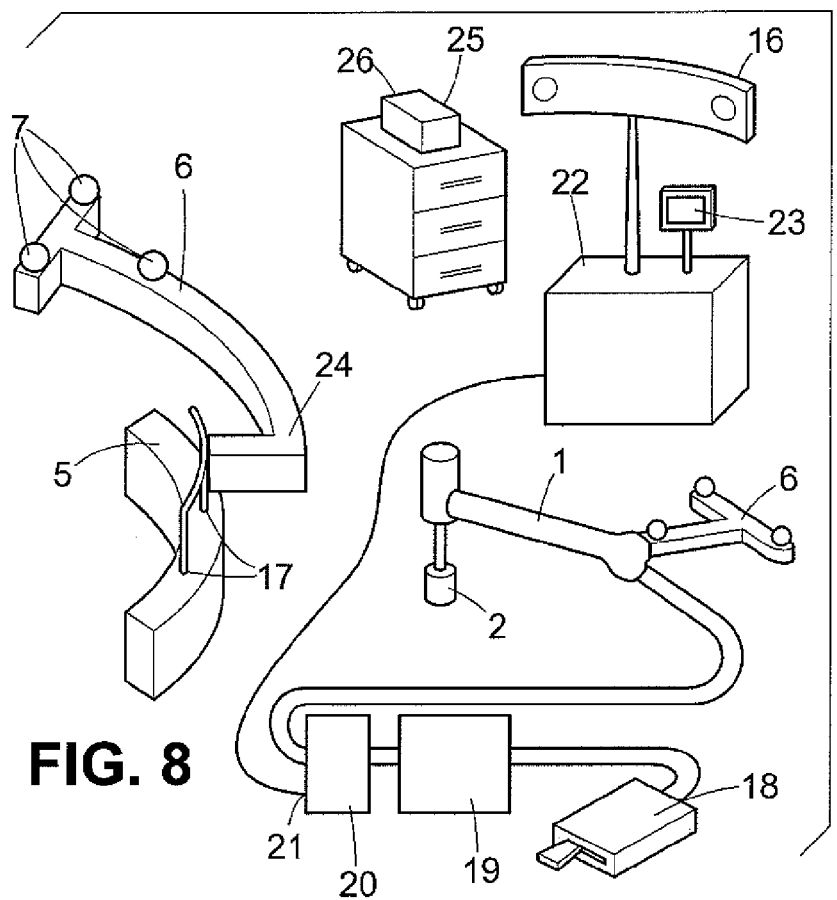

FIG. 8, when viewed in conjunction with FIG. 1, shows a system according to the invention which includes a position measurement systems 16 for measuring the effector position 3 of an effector 2 in a handpiece 1 relative to the reference position 4 of a tissue object 5. FIG. 8 depicts the position measurement system as an optical navigation system 16, with markers 7 implemented as a spherical passive markers 7, whose support 6 is connected to the jawbone by screws via provisional implants 17 or attached to the handpiece 1.

The power of the power converter 19 (drive motor), which is controlled by a power controller 18 (foot switch, hand switch, sensor), for the material-removing or tissue-removing effector 2 can be switched off and/or on and/or reduced to a suitable power level by an attenuation device 20. The attenuation device 20 can also be an integral component of the power converter 19 and can be controlled via an attenuator interface 21.

A control unit 22, preferably a computer with a display 23 (e.g., a display screen with a loudspeaker), is used to read and process the measurement data from the position measurement system 16.

If necessary, the length and the shape of the effector 2 is initially calibrated with a calibration device 24, in the present embodiment a registration point. In conformance with defined criteria, at least one position (position and orientation) of the material or tissue 5 to be removed are identified in the controller or can be defined during operation (online). At least one fitted shape 12 and/or a fitted piece 11 are stored ahead of time or can be defined during operation (online). Alternatively or in addition, criteria for online dynamic computation of at least one fitted shape/fitted piece 11, 12 are stored ahead of time or the corresponding criteria can be defined during operation (online). An object geometry 5 is stored in the controller during operation. The object geometry 5 is either known ahead of time, has been calibrated before use or is measured during the procedure shortly before the tissue is removed. The controller computes, as necessary or quasi-continuously, the effective volume 9, the cut volume 10, selects or calculates the geometry of the fitted piece 11 and the suitable fitted shape 12 and computes the difference geometry 13. The difference geometry is suitably displayed on the monitor and allows the handpiece to be manually arranged and guided, so that the difference geometry can be selectively removed. The controller 22 can switch the power to the effector 2 off and on via the attenuation interface 21 or all attenuate the power, as described above. The already prepared appropriate tilled piece is taken out of inventory 25 (for example by a dental technician or fabricated as a standard shape by a dental supplier) or can be fabricated later (by the dental technician or a machine). The fitted piece is integrated with the fitted shape and suitably finished, wherein the power reduction can be gradually disabled. In the case of a model, the same machining process can be performed on another model or on a patient's tissue.

For producing cavities in hard tissue for implants, the method and a corresponding system are employed as follows.

A measurement marker 7 is attached to the hard tissue 5, so that the position of the hard tissue geometry can be determined or measured quasi-continuously relative to a reference coordinate system 8. The hard tissue 5 can be stationary or freely movable. The position of the hard tissue relative to the measurement markers can be determined by different methods that measure distance or volume or generate surface images. In dentistry and head surgery, a registration template can be attached to the teeth, whereas in other surgical areas surface measurements or a marker registration can be used.

The effector 2 can be, for example, a cutter, a drill or a laser which is guided manually via a corresponding handpiece 1 (but can also be kinematically supported, braked, damped or driven). A measurement marker 7 can also be disposed on the handpiece 1. A position and/or or location measurement system 16 can be used to measure the relative position of the markers and thereby also the marker reference systems 8. Optical, electromagnetic and acoustic navigation systems as well as navigation systems that measure a distance from a surface and/or navigation systems with fixed or variable marker geometries can be used. Optical navigation systems with passive markers can be used with particular ease in dentistry. The geometry and the position of the effector 2 relative to the marker reference system 8 of the handpiece 1 is known ahead of time, or is calibrated by touching a registration point 24 or is calibrated with a registration form. When using a laser handpiece, the focal point can be adjusted accordingly or its position can be measured. In this way, the position 3 of the tissue-removing effector geometry can be measured with the navigation systems quasi-continuously by a coordinate transformation relative to the position 4 of the object tissue 5. Tissue is removed with the effector 2 manually or with the help of a mechanism, wherein—preferably with a computer—the positions and orientation of the tissue-removing effector geometry are logged and an effective geometry 9 is computed from the superposition of the effector geometries. The geometry of the removed tissue volume 10 is computed by intersecting the object geometry 5 with the effective geometry 9. In other words, the geometry of the removed tissue is directly computed. During tissue removal, the physician will try to follow certain criteria. These can include information about the tissue, which can be, for example, identified visually (color, chips), through smell (odors), through tactile information (tissue firmness or changes in the tissue firmness) or acoustically and directly transformed. These can also be information from a preplanning stage, where certain positions, orientations or geometries of the cavities were defined. Cavities can be shaped, for example, for receiving implants. In the simplest case, the cavity is prepared for a predefined implant or transplant. Alternatively, an implant can be selected from a selection of different implants stored in inventory by taking into consideration additional criteria. In this case, the cavity also has to conform to the fitted shape 12 for a fitted piece 11 of the implant. For this reason, a difference body 13 is computed which encloses the tissue that must still be removed to form the fitted shape 12 for the fitted piece 11. This difference geometry 13 is used to optimally arrange and guide the effector 2 for tissue removal. This can be accomplished, for example, by a graphic representation for the physician on a display screen or by controlling a robot-like mechanism. Moreover, an effector geometry body 14 that directly produces a fitted shape 12 can be selected based on the difference geometry. This can be done, for example, with a tissue-removing laser by using a laser handpiece with a cylindrical effector geometry body 14 that is sufficiently transparent so that the tissue-removing laser light cuts a thread into the hard tissue 5 serving as a fitted shape 12 when exiting the effector geometry body 14. After the fitted shape 12 is produced in the tissue 5, the implant or fitted piece 11 can be removed from inventory 25 and directly integrated. To prevent accidental removal of tissue 5 by the manual or kinematically supported arrangement and guidance of the effector 2, which could destroy the optimal fitted shape 12 or does not satisfy the required criteria, the tissue-removing effector power is turned off by computer control, wherein the effector 2 is located outside the difference geometry 13 and/or outside a subset of the joint set of difference geometry 13 and the geometry of the fitted piece 11. Preferably and for safety reasons, the effector power is only switched on when the effector 2 is located inside the difference geometry 13 and/or inside a subset of the joint set of difference geometry 13 and geometry of the fitted piece 11.

To achieve a particularly clean fitted shape 12, the effector power should be decreased with decreasing distance of the effector 2 to the boundary surface between the fitted shape 12 and the difference geometry 13, thus preventing tissue of the fitted shape 12 to be removed accidentally. A suction mechanism for suctioning off odors and vapors and other particles is preferably attached to the handpiece 1.

To produce cavities in the tooth for the application of inlays, onlays or crowns, the method and a corresponding system are employed that are similar to those used for processing bone. However, the fitted piece 11 in the form of an inlay, onlay or a bridge is either taken out of inventory that contains a prepared standard body or is produced by a rapid prototyping process (cut, sintered, etc.) or is fabricated and measured ahead of time by a dental technician. However, material can also be measured and filled in the cavity and/or into a form around the fitted piece.

The method can be used in dentistry also for fabricating or modifying of model work and supra-constructions. In this case, work is performed not only on a patient's tissue, but also on the models or super-constructions, which however can be transferred by using known methods (registration template).

The method can also be used in the knee endoprosthesis, where a large number of cuts has to be set on the bone and matching surfaces have to be cut. In this case, a marker support can be easily screwed to the bone.

The method can also be used in decompression and preparation for screw connections of vertebrae.

For separating hard tissue, the method and a corresponding system are employed as follows. The fitted piece is defined as at least one cut surface or as at least one cut volume. It is not necessary to use a fitted piece.

For separating soft tissue, for example in visceral surgery, the method and a corresponding system are employed as follows, e.g., to set clean cuts in soft tissue 5, for example for separating and removing tissue. The position (position and orientation) 4 of the soft tissue 5 is used, for example via a soft body-GPS, whereby markers 7 are introduced into the soft tissue. The partially independent displacement and movement of tissue structures can be measured by measuring the position of the markers. Clean cuts can be set with a power-controlled effector 2 that separates the tissue. The tissue can also placed into a dimensionally stable matrix 15 ahead of time, pressed or suctioned off, before the tissue-removing power is applied. The matrix 15 itself can also be transparent for energy, so that the cuts can be suitably guided through the matrix. The cutting tool is here preferably a laser, which is scanned over the tissue and automatically measures the cut position. The power is added only at the planned cut edges or cut surfaces. The shaping matrix 15 can thereby be made of a light-conducting material.

The process of automatic calibration is explained in more detail with reference to FIG. 9.

Figure 9:
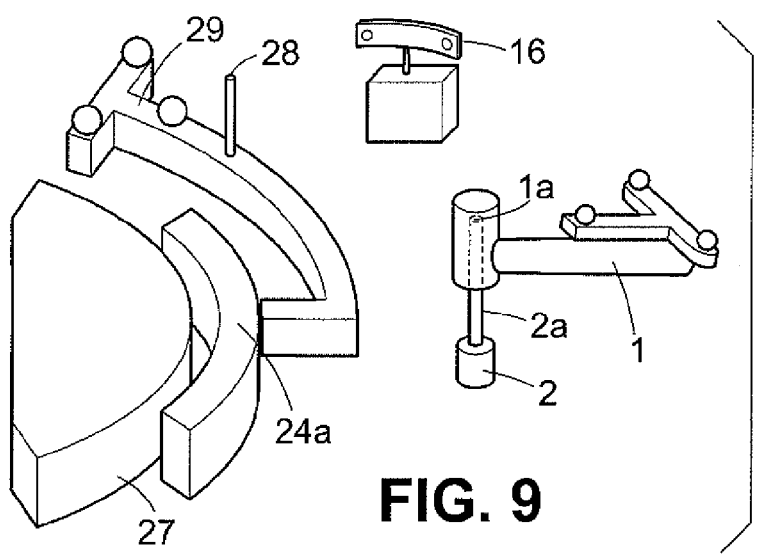

FIG. 9 shows a handpiece (1) with a tool receptor (1*a*) and a chucked tool (2*a*), whereby the position (position and orientation) of the tool effector (2) is to be measured. Also visible is the registration point (24*a*), the work volume (27) and the calibration body (28) which in the present embodiment is implemented as a pin. The position is measured by the position measurement system (16) which also stores the transformation matrices relative to a reference coordinate system (29).

The figure shows this as an optical navigation system with passive reflectors.

After the system is turned on, the user receives a signal to calibrate the handpiece (1). The user places the handpiece (1) on the fitted piece. He can then clamp a tool (2*a*), for example a drill. Before entering the work volume (27), the user touches with a tool tip the registration point (24*a*) and waits for the registration signal. The user then navigates in the work volume (27). If he places the instrument outside the work volume (27), then he has to touch the registration point (24*a*) again when he reenters the work volume (27). The same applies for a tool change.

Figure 10:
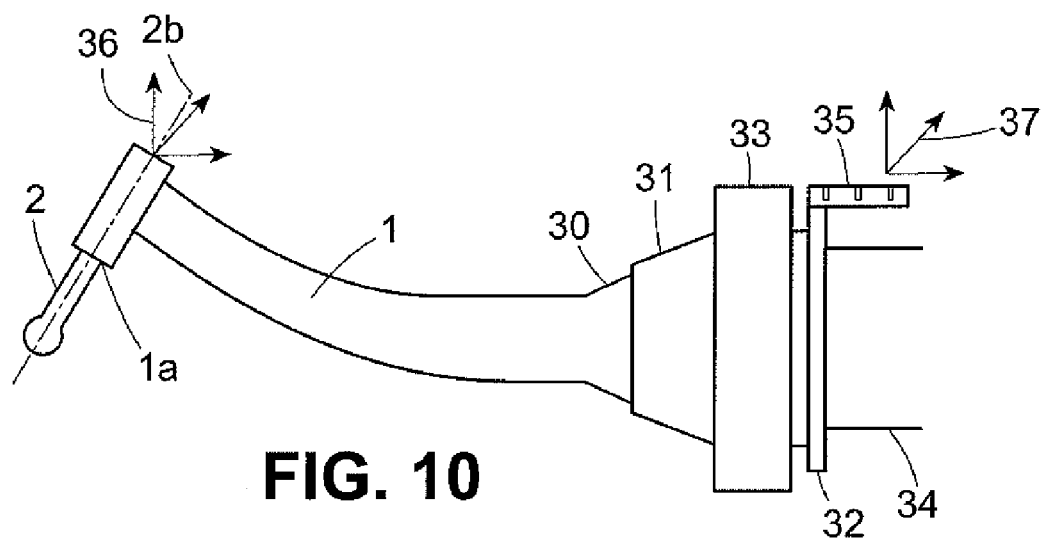

FIG. 10 shows a handpiece 1 with an effector receiver 1*a*, such as a chuck, for clamping an effector 2, such as a drill.

The effector receiver 1*a* has an effector reference position 36, which defines the zero position and the orientation of an effector 2 located in the effector receiver 1*a*. A handpiece marker support 32 with a handpiece marker 35 can be attached to the handpiece 1 in such a way that the handpiece marker 35 can be attached and affixed in at least one predetermined position (position and orientation) relative to the effector reference position 36.

The handpiece marker support 32 with the handpiece marker 35 can either be permanently or removably affixed to the handpiece 1. The handpiece 1 itself can be the hand piece marker support 32.

Figure 11:
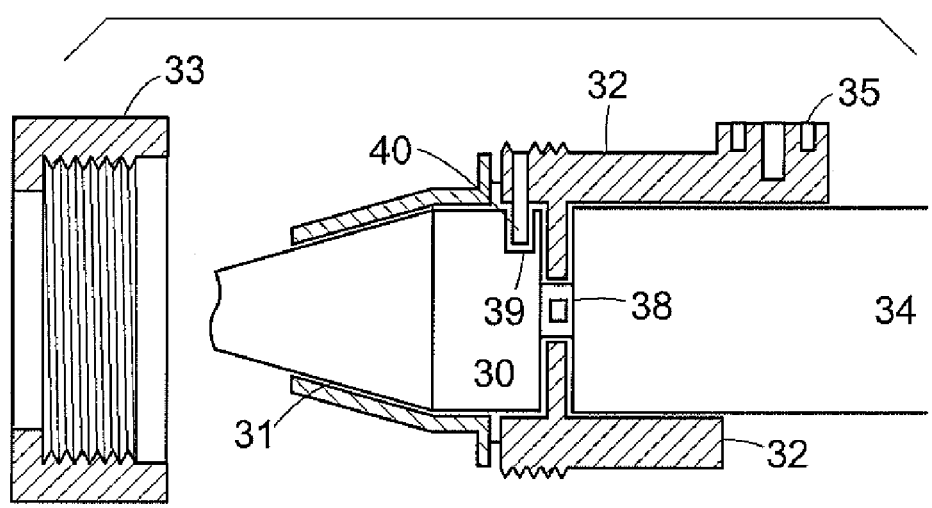

FIG. 11 shows a type of the aforedescribed attachment of the handpiece II. marker support 32 to the handpiece 1. A hollow frustoconical coupling cone 31 is placed over the handpiece cone 30, serving as a counter bearing for the clamping of the handpiece marker support 32 with the handpiece 1. The inside diameter of the coupling cone 31 is sufficiently large to be pushed over the effector receiver 1*a* to the handpiece cone 30, but is smaller than the outside diameter of the handpiece cone 30 at its greatest circumference. The handpiece marker support 32 is affixed to the handpiece 1 with a union nut 33 that has a sufficiently large inside diameter so as to be pushed over the effector receiver 1*a* and the handpiece 1, but is smaller than the outside diameter of the coupling cone 31 at its greatest circumference. The interior thread of the union nut 33 is screwed on the outside thread of the marker support 32.

Figure 12:
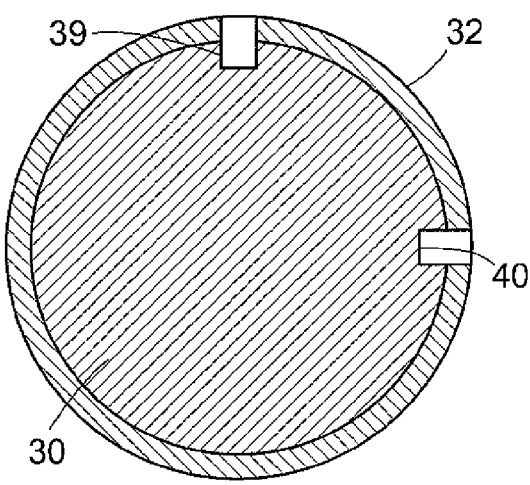

FIG. 12 shows a handpiece cone 30 with at least one groove formed as a recessed opening 39 for insertion of at least one projection 40 formed as a registration spring which is attached on the side of the handpiece marker support 32. In one embodiment, a projection 40 in form of a pin is inserted into a bore applied laterally in the outside thread. Pin 40 and recess 39 must have a snug fit to prevent rotation of the marker support with respect to the effector reference position 37.

In order to be able to optimally mark the orientation of an angular handpiece 1 for the upper and lower jaw, the openings 39 in the form of grooves should be applied a second time, this time rotated by 180 degrees about the drive axis. Instead of implementing the pin 40 in the marker support 32 and the groove 39 in the cone 30, the pin 40 can also be implemented in the cone 30 and the groove 39 in the support 32.

Figure 13:
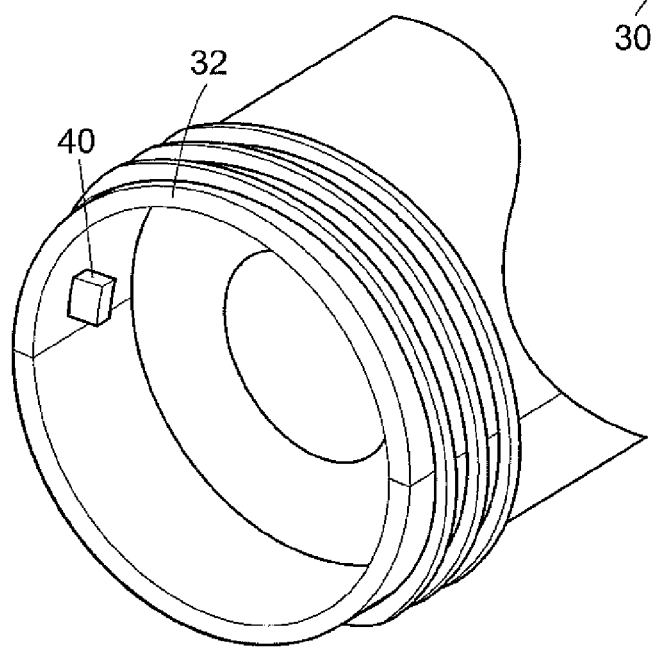

FIG. 13 shows an embodiment of the handpiece marker support 32 which consists of two halves which when joined produce the same geometry as in FIG. 11. In this embodiment, the recess 39 in the handpiece 1 can be limited to a horizontal drilling, since the two halves can be pushed on, so that the pin 40 formfittingly enters the bore 39. Advantageously, the two halves can be implemented as a plug connection. Since the union nut 33 affixes the two halves about the handpiece, the coupling cone 31 can be eliminated in this embodiment.

Figure 14:
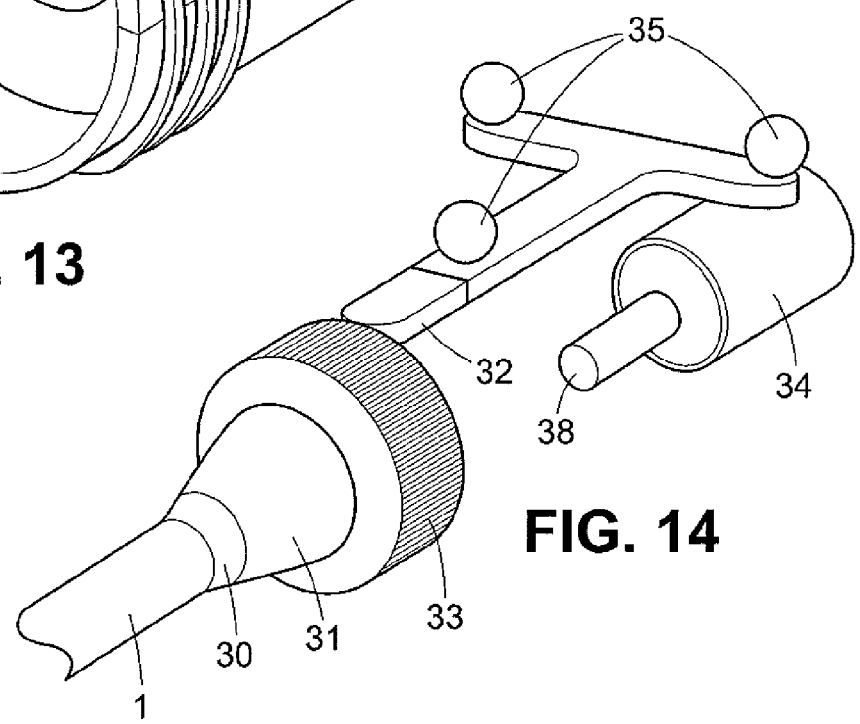

FIG. 14 shows a handpiece 1 with a marker support 32 which is fixedly connected with the handpiece 1 by the coupling cone 31 and the union nut 33 at a predetermined position. A marker 35 made of reflecting glass spheres, which can be used as signal reflectors in an optical coordinate measurement system, is disposed on the marker support 32.

The marker 35 is generally a number of points, figures or bodies which have a known predetermined position (position and special orientation) relative to each other as well as relative to a multi-dimensional position reference coordinate system 37, and whose position relative to at least one position measurement coordinate system can be optionally determined. Different measurement methods (optical, acoustic, electromagnetic, radar, laser, line camera, area cameras, video sequences, 3-D surface cameras, 3-D laser cameras, 3-D radar methods, etc. with signaled transmitting, signal receiving and signal reflecting points, figures or bodies) can be used.

Alternatively, the marker can be implemented as a flange for receiving a measurement sensor in a known handpiece reference position 37. The handpiece reference position 37 (position and orientation) of the handpiece marker 35 and hence also of the effector reference position 36 can be determined with at least one position measurement system relative to the reference coordinate system of the respective position measurement system.

The handpiece marker 35 can be applied to or recessed in the handpiece marker support 32 and/or formed by a portion of the geometry of the handpiece marker support 32.

The handpiece 1 is initially marked by applying the handpiece marker 35. If the coupling mechanism is used, then the handpiece marker support 32 together with the handpiece cone 30 is affixed with pins via the support spring 40 and the conical recess 39. The coupling cone 31 and then the union nut 33 are subsequently pushed over the handpiece, and the coupling cone 31 with the handpiece marker support 32 is tightened until reaching a final stop and/or until the support spring 40 is inserted into the cone recess 39 as far as possible. The position of the handpiece 1 can now be measured via the handpiece marker 35 by using a position measurement system. The drive 34 can be connected later with the coupling 38.

The method can also be used outside the medical field, for example when removing material in manufactures or trade businesses (joiner, carpenter, wood ship building) or by do-it-yourselfers, where fully automatic computer-controlled processing machines cannot be used. This can be the case, because the machines are either too large or too expensive or cannot be acquired at all. In this case, the methods and a suitably equipped manual processing machine (electrically operated do-it-yourself equipment) can provide a result which is comparable to results obtained with a numerically controlled automatic machine. An exemplary application is here shape-grinding for restoring antique cars or sanding a glass-fiber-reinforced plastic hull of an old sailboat. A standard body is here defined on the basis of known old projections or technical drawings. The reference point of a coordinate measurement device, for example of a difference-GPS or an optical or laser- or radar-based coordinate measurement device or a measurement arm, is attached to the processed object. The effector geometry, for example of the grinding wheel, is either known or is calibrated in a form. The effector position of the tissue-removing effector geometry of the machine (grinder, cutter, polishing head) is continuously determined and the power (RPM) of the machine during grinding is defined so that the machine power is controlled as a function of the distance between actual position of the tissue-removing effector and the surface position of the standard geometry. For example, the machine operates at full power up to a distance of 2 mm from the surface and is then controlled with decreasing power to a distance of 0 mm to the surface. Other control methods can be employed depending on the application. The position of the standard body or the standard geometry relative to the object geometry can be achieved by determining the position of the object body by touching at least one symmetry axis (e.g., tip of the bow, corners of the stern, rudder base on the keel) with a tactile position sensor or by measuring the surface and registering a particularly distinct partial geometry of the object body by averaging, measuring the surface and determining a symmetry.

The method can also be used to later produce in an inaccurately and asymmetrically troweled surface a surface that satisfies specific optimization criteria, such as a low air or water resistance or symmetry with minimum material removal, etc.

The method can also be used to later insert planks or ribs at the optimal position, whereby the object body is then prepared for a snug fit with a fitted piece or the fitted piece is prepared before insertion in the object body.

The materials to be processed can be, for example, metal, glass, ceramic, wood, plastics, depending on the different fields of application.

The invention is not limited to the illustrated embodiments. Instead, it is possible to realize additional embodiments by a combination of the aforedescribed means and features, without deviating from the scope of the invention.

LIST OF REFERENCE NUMERALS 1 handpiece
1a tool receptor
2 effector
2a tool
2b effector axis
3 effector position 4 reference position
5 tissue object
6 marker support
7 marker
8 marker reference system
9 effective volume/geometry
10 cut volume/geometry
11 (geometry of the) fitted piece
12 fitted shape/geometry
13 difference volume
14 effector geometry body
15 dimensionally stabilizing matrix
16 position measurement device
17 preliminary implants
18 power controller
19 power converter
20 attenuation device
21 attenuation interface
22 controller
23 display (screen)
24 calibration device
24a registration point
25 bearing/support
26 processing machine
27 work volume
28 calibration body
29 reference coordinate system
30 handpiece cone
31 coupling cone
32 handpiece marker support
33 union nut
34 effector drive
35 handpiece marker
36 effector reference system
37 handpiece reference system
38 drive coupling
39 opening
40 projection

What is claimed is:

1. A method for removing and processing material with at least one effector, wherein the effector defines a volume and has a predetermined geometry, the method comprising:

removing and processing material from an object with the effector, wherein the removing and processing comprises:

manually guiding the effector in relation to the object;

determining, using a navigation system, position and orientation of the effector in relation to at least one reference body as the effector removes material from the object;

storing data representative of the position and orientation of the effector in relation to the reference body as the effector removes the material from the object; and supplying at least one of power and parameterization control commands to the effector as a function of at least one of a predetermined work volume for the object, volume of the material removed from the object and volume of residual material in the work volume, wherein the removed material volume and the residual material volume are determined based on the volume and the geometry of the effector and the position and orientation of the effector data.

2. The method of claim 1 further comprising:

measuring position and geometry of a removed portion of the object resulting from the removal of the material from the object by the effector; and storing data representative of the measured position and geometry of the removed portion of the object for use in performing additional processing operations on the object or other objects.

3. The method of claim 1 further comprising:

measuring the position of the effector relative to the position of the object quasi-continuously during a defined time interval; and computing geometry of the material removed by the effector based on the measurement of the position of the effector during the defined time interval.

4. The method of claim 3 further comprising:

obtaining 3-D-surface image data of the object using a 3-D-scanner; and computing the geometry of the removed material using the 3-D surface image data.

5. The method of claim 1 further comprising:

computing position and geometry of material to be removed from the object based on at least one of (i) predetermined length and geometry of a desired fitted object shape, and (ii) position and geometry of the material removed from the object; and using the position and geometry of the material to be removed for arranging and guiding the effector.

6. The method of claim 5 further comprising:

switching the power of the effector off no later than when the geometry of the removed material and the geometry of the fitted object shape overlap.

7. The method of claim 5 further comprising:

controlling the power supplied to the effector at least within the geometry of the material to be removed based on the distance of at least one of (i) the position and (ii) the geometry of the effector to a boundary surface between the material to be removed and the desired fitted object shape.

8. The method of claim 5 further comprising:

supplying power to the effector as a function of an energy-transporting shaping matrix, and without changing the position of the effector, for obtaining at least one part of the desired fitted object shape.

9. The method of claim 5 further comprising:

computing the desired fitted object shape based on at least one of (i) medical criteria; (ii) already removed material; (iii) criteria for producing the desired object shape and a fitted piece; and (iv) criteria for integrating the desired fitted object shape and the fitted piece.

10. The method of claim 9 further comprising:

measuring the position of the geometry of the effector quasi-continuously; and storing data representative of the position of the effector geometry as a function of time of the measurement, wherein the effector geometry is at least one of (i) known, (ii) measured as needed, and (iii) quasi-continuously measured, wherein the effector geometry is stored with at least one of (i) the time of the measurement, and (ii) the position of the effector volume.

11. The method of claim 9 further comprising:

using the geometry of the fitted piece for at least one of measuring a material quantity and fabricating another fitted piece.

12. The method of claim 1 further comprising:
computing an effective volume at least one of as needed and quasi-continuously from spatial overlap of the effector volume in the measured positions; and
at least one of
(i) forming, at least one of as needed and quasi-continuously, an intersecting volume from the intersecting set of effective volumes with an object volume, and
(ii) computing a geometrical description of the intersecting volume,
wherein at least one of (i) the position of the object volume relative to the effective volume is at least one of known and measured; and (ii) the intersecting volume description is used, at least one of as needed or quasi-continuously, for computing the geometry of a fitted piece, wherein the geometry of the fitted piece is changeable for satisfying at least one of medical criteria, criteria relating to fabricating and criteria relating to integrating the fitted piece, and wherein the description of the intersecting volumes corresponds to the shape of the fitted piece.

13. The method of claim 1 further comprising:
using at least one table with at least one geometrical description of a fitted piece as a standard body.

14. The method of claim 13 further comprising:
selecting the standard body from a standard body table for satisfying an optimization criterion, wherein the standard body corresponds to a sole entry of a fitted piece in the table; and
providing an inventory including prefabricated standard bodies corresponding to the table of the fitting bodies, wherein the prefabricated standard bodies require at least one of minor finishing machining and no finishing machining.

15. The method 1 further comprising:
computing a difference volume between at least one of (i) a selected fitted piece and (ii) a computed fitted piece, and an actual intersecting volume.

16. The method of claim 1 further comprising:
switching the supply of power to the effector off when the effector is located outside the geometry of a fitted piece.

17. The method of claim 1 further comprising:
switching the supply of power to the effector on when the effector is located inside the geometry of a fitted piece.

18. The method of claim 1, wherein the object is soft, the method further comprising:
substantially dimensionally stabilizing the object using a matrix having at least one option for predetermined supply of power and parameterization control commands to the effector.

19. The method of claim 1 further comprising:
arranging and guiding the effector using a difference volume geometry.

20. The method of claim 1 further comprising:
suctioning at least one of removed particles, vapors and odors off the object during removal of material by the effector.

21. The method of claim 1 further comprising:
measuring 3-D surface geometry of the object using the effector.

22. The method of claim 1, wherein the effector is a laser and wherein the geometry of the effector is determined based on at least one of an exchangeable light-conducting positive effector geometry body and an opaque negative effector geometry body.

23. The method of claim 1 further comprising:
measuring geometry of a portion of the object from which material has been removed at least one of directly and by an impression, wherein the measuring by impression is performed using at least one of a volume-image-forming method and a method that forms a surface image.

24. The method of claim 1 further comprising:
performing a first material removal operation on a model; and
measuring position and shape of the removed material for use in the removal of material from at least one of the model, a different model, the object and another object.

25. The method of 1 further comprising:
determining a geometrical model of the removed material from the object using at least one of effective geometry, cut geometry, difference geometry and a 3-D surface scanner;
storing the geometrical model; and
using the geometrical model for removal of material from at least one of the object, another object and a model, wherein the use of the geometrical model includes mirror-imaging a positive geometry of a cut out from the object into a negative geometry.

26. The method of claim 1 further comprising:
displaying on a graphical display position and geometry of the material still to be removed from the object, based on position and geometry of the material removed and predetermined position and geometry of a desired fitted object shape;
displaying, at least one of on a graphical display and acoustically, information about the position of the effector relative to a boundary surface between the fitted object shape and the material still to be removed; and
using the position information of the effector for at least one of manually and kinematically arranging and guiding the effector, wherein the position information is outputtable via an interface for controlling a placement and guidance mechanism for the effector.

27. The method according to claim 1 further comprising:
at least one of measuring and computing position and orientation of a handpiece T_HAND, wherein the handpiece includes a tool receptor for the effector;
storing a transformation matrix HAND_T_SPANN between the handpiece and the tool receptor; and
providing a transformation matrix SPANN_T_WERK between the tool receptor and the effector, wherein the transformation matrix SPANN_T_WERK is a missing positional degree of freedom, wherein the missing degree of freedom is at least one of length and a registration point P-REG.

28. The method of claim 27, wherein the registration point P-REG is arranged such that the handpiece passes the registration point before entering the work volume.

29. The method of claim 27 further comprising:
at least one of using and transmitting computed position and orientation T_WERK of the effector, only if the transformation matrix HAND_T_WERK between the handpiece marker and the tool effector is registered and stored.

30. The method of claim 27 further comprising:
deleting the transformation matrix HAND_T_WERK between the handpiece marker and the effector and a registration, if the position T_WERK of the effector at least one of (i) could not be measured or computed during a predefined time interval, and (ii) is not located in the work volume during a predefined time interval.

31. The method of claim 27 further comprising:
automatically computing the missing positional degree of freedom of the transformation matrix HAND_T_WERK, if the effector appears to be located during a predefined time interval inside a small known tolerance volume around the registration point.

32. The method of 31 further comprising:
computing the missing relevant positional degree of freedom of the transformation matrix SPANN_T_WERK using a statistical evaluation process, as long as the effector appears to be continuously located during a predefined time interval inside a small known tolerance volume around the registration point; and
storing the transformation matrix SPANN_T_WERK.

33. The method of claim 27 further comprising:
signaling at least one of the state of registration, start of computation of the registration and end of the computation of the registration; and
signaling at least one of a parameter of the computation of the registration and a computed relevant degree of freedom.

34. The method of claim 27 further comprising:
estimating a transformation matrix HAND_T_SPANNKAL between the handpiece and the tool receptor at least one of (i) entirely and (ii) entirely with the exception of an irrelevant position degree of freedom, such that deviations between HAND_T_SPANN and HAND_T_SPANNKAL are located inside tolerance limits and outside unfavorable calibration tolerances; and
providing a calibration tool configured as an alignment pin.

35. The method of claim 34 further comprising:
signaling at least one of a state of calibration, start of the calibration, end of the calibration and a parameter of the calibration result.

36. The method of claim 27 further comprising:
at least one of using and transmitting the transformation matrix HAND_T_SPANN between the handpiece and the tool receptor, only if the transformation matrix HAND_T_SPANN has been calibrated and stored.

37. The method of claim 27 further comprising:
deleting the transformation matrix HAND_T_SPANN between the handpiece and the tool receptor upon the occurrence of an event, wherein the event includes a first use; and
automatically computing the transformation matrix HAND_T_SPANN when the tool receptor during a predefined time interval is located at a position where the tool receptor subsequently receives a calibration tool.

38. The method of claim 27 further comprising:
computing the transformation matrix HAND_T_SPANN by a statistical evaluation process, as long as during a predefined time interval the tool receptor is in a position where the tool receptor appears to have received a calibration tool; and
storing the transformation matrix HAND_T_SPANN.

39. The method of claim 1, wherein the work volume is defined such that the effector is operable for removing substantially all of the material from the work volume during an application of the effector, without removing the effector from the work volume.

40. A system for at least one of removing and processing material comprising:
at least one effector defining a volume and having a predetermined geometry coupled to a handpiece and operable to be manually guided in relation to an object to remove material from the object;
a navigation system for determining position and orientation of the effector as the effector removes material from the object;
a control unit coupled to the handpiece and the navigation system;
a first marker support with first markers arranged on the handpiece and detectable by the navigation system;
a second marker support for securing to the object and including second markers detectable by the navigation; and
wherein the control unit supplies at least one of power and parameterization control commands to the effector as a function of at least one of a predetermined work volume for the object, volume of the material removed from the object and volume of residual material in the work volume, and wherein the control unit determines the removed material volume and the residual material volume based on the volume and the geometry of the effector and data representative of the position and orientation of the effector as the effector removes the material from the object.

41. The system of claim 40, wherein the control unit is coupled to a position measurement system and a display, and further comprising:
a power controller, a power converter and an attenuation device with an attenuation interface coupled to one another between the control unit and the handpiece.

42. The system of claim 40, wherein the second marker support includes a calibration device.

43. The system of claim 40, wherein the control unit disconnects supply of power to the effector, via the attenuation interface or the attenuation device, not later than when the control unit determines that an overlap between removed material and a desired fitted object shape occurs.

44. The system of claim 40, wherein the control unit controls the supply of power to the effector via the attenuation interface or the attenuation device at least inside the geometry of the material still to be removed from the object, based on the distance from at least one of the position of the effector and the effector geometry to the boundary surface between the material to be removed and the desired fitted object shape, and wherein the effector is used for 3-D-surface geometry measurements of the object.

45. The system of claim 40, wherein the first markers are spherical passive marks.

46. The system of claim 40, wherein the handpiece defines at least one opening for attachment to a third marker support, wherein the opening is shaped to provide for a formfitting engagement with a projection of the third marker support when the third marker support is installed on the handpiece.

47. The system of claim 46, wherein the handpiece has a second opening rotationally offset by 180 degrees about a drive axis of the handpiece and for receiving a projection for attaching the third marker support when the handpiece is rotated by 180 degrees.

48. The system of claim 46, wherein the projection of the third marker support is shaped for formfitting insertion into the handpiece opening and is attachable in at least one predefined position and orientation relative to an effector reference system,
wherein a handpiece marker on the handpiece marker support is at least one of recessed in the handpiece marker support and formed by a portion of the geometry of the handpiece marker support, and wherein a drive for the effector is coupled to the effector by a coupling.

49. The system of claim 48, wherein the handpiece marker comprises a set of at least one of points, figures and bodies having at least one of a position and orientation relative to at least one of each other and a pre-determined multi-dimensional position reference coordinate system, wherein the position of the handpiece marker relative to at least one position measurement coordinate system is determined by at least one of optical, acoustic, electromagnetic, radar, laser, line camera, area cameras, video sequences, 3-D-surface cameras, 3-D-laser cameras and 3-D-radar processes using at least one of signal-transmitting, signal-receiving and signal-reflecting points, figures and bodies.

50. The system of claim 48, wherein the handpiece marker is a flange for receiving a measurement sensor having a predetermined handpiece reference position, and wherein a handpiece reference position of the handpiece marker and the effector reference position are determinable by using at least one position measurement system relative to the reference coordinate system of the corresponding position measurement system.

51. The system of claim 48, wherein the handpiece marker is releasably secured to the handpiece marker support.

52. The system of claim 46, wherein position of the third marker support is fixed with at least one of a union nut and a union cone.

53. The system of claim 40, wherein the handpiece has at least one projection for attachment to a third marker support, wherein the projection is formed to provide for a formfitting engagement with an opening of the third marker support when the third marker support is installed on the handpiece.

54. The system of claim 53, wherein the handpiece marker is releasably secured to the handpiece marker support by at least one of latching and interlocking.

55. The system of claim 40, wherein the effector is manufactured from at least one of light-weight, dimensionally stable, disinfectable and sterilizable material.

56. The system of claim 40, wherein the effector is for removing tissue.

57. The system of claim 40, wherein the effector is for removing at least one of metal, glass, ceramic, wood and plastic.

* * * * *